United States Patent [19]

Rubin

[11] Patent Number: 4,843,095

[45] Date of Patent: Jun. 27, 1989

[54] FREE FATTY ACIDS FOR TREATMENT OR PROPYHLAXIS OF RHEUMATOID ARTHRITIS

[75] Inventor: David Rubin, San Diego, Calif.

[73] Assignee: Century Laboratories, Inc., Port Washington, N.Y.

[21] Appl. No.: 82,701

[22] Filed: Aug. 7, 1987

[51] Int. Cl.$^4$ ............................................. A61K 31/23
[52] U.S. Cl. ................................ 514/558; 514/559; 514/560
[58] Field of Search ......................... 514/558, 559, 560

[56] References Cited

U.S. PATENT DOCUMENTS

| | | | |
|---|---|---|---|
| 4,302,447 | 10/1981 | Horrobin | 424/145 |
| 4,472,432 | 9/1984 | Iwamura et al. | 424/318 |
| 4,512,996 | 4/1985 | Somers | 514/304 |
| 4,526,902 | 7/1985 | Rubin | 514/560 |

FOREIGN PATENT DOCUMENTS 2033745  5/1980  United Kingdom .
1604554 12/1981  United Kingdom .

OTHER PUBLICATIONS

"Effects of Manipulation of Dietary Fatty Acids on Clinical Manifestations of Rheumatoid Arthritis", *The Lancet*, Jan. 26, 1985, pp. 184–187.

"Dietary Fish Oil Augments of the Induction of Arthritis in Rats Immunized With Type II Collagen[1]", *The Journal of Immunology*, vol. 132, No. 2, Feb., 1984, pp. 725–729.

"Dietary Fish Oil Modulates Macrophage Fatty Acids and Decreases Arthritis Susceptibility in Mice", *Journal of Experimental Medicine*, vol. 162, Oct. 1985, pp. 1336–1349.

"Fish-Oil Fatty Acid Supplentation in Active Rheumatoid Arthritis", *Annals of Internal Medicine*, Apr., 1987, vol. 106, No. 4, pp. 497–503.

*Primary Examiner*—Curtis R. Davis
*Attorney, Agent, or Firm*—Browdy and Neimark

[57] ABSTRACT

Free fatty acids form fish oil, DHA and EPA, are useful in treating rheumatoid arthritis. The free fatty acids were an order of magnitude more effective in treating arthritis than unhydrolyzed fatty acids derived from fish oil.

9 Claims, No Drawings

FREE FATTY ACIDS FOR TREATMENT OR PROPYHLAXIS OF RHEUMATOID ARTHRITIS

FIELD OF THE INVENTION

The present invention relates to the use of free fatty acids which can be used to treat or provide effective prophylaxis against rheumatoid arthritis.

BACKGROUND OF THE INVENTION

Rheumatoid arthritis is a serious, often crippling, disease characterized by pain and locomotor dysfunction. This sort of pain and dysfunction are among the most common and frustrating afflictions. The gravity of this disease has led to the investigation and/or adoption of a wide range of drugs for its alleviation. Aspirin has been commonly used since the turn of this century. Other major drugs used to treat arthritis include indomethacin, other salicylates, phenylbutazone, steroids, and gold. Other compounds which have been used to treat arthritis are fenoprofen, ibuprofen, naproxen, sulindac, and tolmetin.

While the known compounds can offer anti-inflammatory, antipyretic, and analgesic effects, and have proven helpful in the management of rheumatoid arthritis in many patients, when combined with other modalities such as proper rest, exercise, physical therapy, and surgery, they are less than ideal. Many of these medications exhibit serious side effects with many patients, particularly gastrointestinal damage and renal toxicity. None of these materials is universally useful in treating rheumatoid arthritis, as some patients will respond to one material while others respond favorably only to others.

Cocaine and cocaine free base have also been employed in the management of rheumatoid arthritis. Unfortunately, cocaine and cocaine free base are widely abused, and it is highly unlikely that the regulatory and drug enforcement agency issues will ever be resolved to a point that cocaine or its free base can be available on as widespread a basis as would be required for their use in the treatment of sufferers of rheumatoid arthritis.

Somers, in U.S. Pat. No. 4,512,996, disclose the use of benzoylecognine and/or benzoylnorecognine for treating rheumatoid arthritis. These compounds are formed by mammals as a metabolite of cocaine.

Horrobin, U.S. Pat. No. 4,302,447, discloses the use of gamma-linolenic acids and related materials to treat schizophrenia, obesity, menstrual disorders, skin disorders, and other conditions.

Rubin, U.S. Pat. No. 4,584,320, discloses a method for treating asthma, nasal congestion, and anaphylactic shock by administration of 8,11,14,17-eicosatetraenoic acid.

Iwamura et al., U.S. Pat. No. 4,472,432, disclose the use of a compound of the formula $CH_3(CH_2)_nCH=CHCO_2H$ wherein n is 10, 12, 14, or 16, for treating diabetes or improving lipid metabolism. The compounds can be separated from freshwater clams by subjecting the freshwater clams to extraction with hot water and/or an aprotic solvent.

The active ingredients in fish oil are (all-Z)-5,8,11,14,17-eicosapentaenoic acid (hereinafter EPA) and 22:6 omega3-docosahexaenoic acid (hereinafter DHA). EPA and DHA are known to be precursors in the biosynthesis of the prostaglandin $PGE_3$.

It is disclosed in British Pat. Nos. 1,604,554 and 2,033,745 that EPA can be used to treat effectively, or to provide effective prophylaxis against, thromboembolic- conditions such as myocardial infarctions, strokes, or deep vein thrombosis during surgical operations. These patents disclose the extraction of EPA from fish oil such as cod liver oil or menhaden oil. The EPA may be administered by replacing butter or ordinary margarine by a special margarine formulated to that in normal usage the recipient would receive the required amount of the EPA.

This process has not achieved widespread attention, despite the fact that it uses a natural substance which can readily be incorporated into the daily diet. One reason may be due to the difficulty of efficiently separating EPA from natural fish oils to obtain a pure product at reasonable cost. Another reason may be that the effects of administration of EPA are not as dramatic as anticipated.

Rubin U.S. Pat. No. 4,526,902 teach the use of EPA and/or DHA in combination with linoleic acid, $\gamma$-linolenic acid and/or DHLA to obtain enhanced effects in the treatment of or prophylaxis against thromboembolic conditions. This patent discloses that the acids may be administered in free acid form or in the form of their physiologically acceptable salts, esters or amides.

Prostaglandins are a family of substances showing a wide diversity of biological effects. Prostaglandins of the 1-, 2-, and 3-series, respectively, incorporate one, two, or three double bonds in their basic 20-carbon carboxylic fatty acid structure which incorporates a 5-member cyclopentene ring.

The 1-series of prostaglandins are strong vasodilators, and inhibit cholesterol and collagen biosynthesis, as well as platelet aggregation. On the other hand, the 2-series prostaglandins are known to enhance platelet aggregation, cholesterol, and collagen biosynthesis, and also to enhance endothelial cell proliferation. The main effect of the 3-series prostaglandins, particularly $PGE_3$, is the suppression of the 2-series prostaglandins.

The precursor of the 2-series prostaglandins is arachidonic acid ((all-Z)-5,8,11,14-eicosatetraenoic acid). Dihomo-$\gamma$-linolenic acid (DHLA) is the precursor for the 1-series prostaglandins, and, as indicated hereinabove, EPA and DHA are precursors for the 3-series prostaglandins.

It is believed that EPA and DHA are effective precursors for prostaglandin $PGE_3$, which suppresses the 2-series prostaglandins. Additionally, EPA and/or DHA itself competes with arachidonic acid on the same enzymatic system and thus inhibits the biosynthesis of 2-series prostaglandins. This inhibition of the 2-series prostaglandins results in an increase of the ratio of $PGE_1:PGE_2$.

It is believed that in rheumatoid arthritis, there are evidences of extremely low levels of $PGE_1$ and high levels of $PGE_2$. Further, the anti-inflammatory effect of corticosteroids and the pain killing effect of aspirin are believed to be due to their suppression of $PGE_2$ formation.

It has recently been discovered that substances in fish oils are effective in treating arthritis in animals. It is believed that the EPA and/or DHA present in the fish oils is the effective agent in fish oil.

Leslie et al., in J. Exp. Med. 1985, 162 1336–1349, disclose that dietary fish oil can be used to decrease the susceptibility to arthritis in mice. However, the fish oil was administered in the unhydrolyzed state.

Prickett et al., in J. Immun. 1984, 725–729, disclose that a fish oil diet, enriched in highly unsaturated long chain fatty acids, provided an increased incidence of collagen-induced arthritis in rats as compared with rats receiving a diet containing beef tallow containing less than 0.05% EPA.

Kremer et al., in Lancet Jan. 26, 1985, 184–187, disclose that the manipulation of fatty acids in the diet can be beneficial in treating arthritis in animals. In this case, the fatty acids were supplemented with EPA from Max-EPA capsules, which contain unhydrolyzed fish oil EPA.

Kremer et al. in Ann. Int. Med. 1987, 106 (4), 497–503, disclose that fish-oil dietary supplements were effective in subjective alleviating active rheumatoid arthritis and reducing neutrophil leukotriene B4 production.

SUMMARY OF THE INVENTION

It is an object of the present invention to produce a composition which can be used to treat rheumatoid arthritis.

It is another object of the invention to provide a compound for prophylaxis against rheumatoid arthritis.

These and other objects of the present invention are obtained by the use of free fatty acids obtained from fish oil. The effects of the fish oil on patients suffering from rheumatoid arthritis was attributed to the fact that the fish oil would interfere with the production of $PGE_2$. However, there was an enormous difference between the effect of the fish oil in the form of the naturally-occurring triglyceride and the effect of the free fatty acid.

It would appear that the triglyceride, even if completely hydrolyzed by pancreatic lipase, becomes re-esterified soon after crossing the intestinal walls. This triglyceride migrates to the adipose tissues surrounding the body, so that very little of the fatty acid is bioavailable. The free fatty acids, on the other hand, are readily absorbed, and are conjugated to serum albumin and thus are available to compete with arachidonic acid in different sites of the organism.

DETAILED DESCRIPTION OF THE INVENTION

Rheumatoid arthritis can be treated according to the present invention by administering to a patient suffering from rheumatoid arthritis the free fatty acid EPA or DHA or a mixture thereof. Although when extracted from fish oils these acids are generally present in the amounts of approximately 35% EPA/65% DHA, the acids can be administered in any combination thereof. The dose of the free fatty acids needed for therapeutic or prophylactic effect will vary with the route of administration and the nature and severity of the condition being treated, but it will generally be at least 0.5 gram, and preferably from 1.5 to 5 grams, per day. This is the dosage for an average 70 kg adult male, and the dose for other patients will vary pro rata according to the weight of the patient, i.e., about 20–40 mg/kg.

The EPA and/or DHA need not be administered as the free fatty acids per se, but may be used in the form of their pharmaceutically acceptable salts. The preferred salts are the sodium or potassium salts, or any other pharmaceutically acceptable solid salt, as these are suitable for making into orally ingestible tablets.

While it is preferred to administer the free fatty acids of the present invention orally, as this is a convenient route for routine administration, the free fatty acids may be administered by any route by which it may be successfully absorbed, e.g., parenterally (i.e., subcutaneously, intramuscularly, or intravenously), rectally, vaginally, or topically, for example, as a skin ointment or lotion.

While it is possible for the free fatty acids to be administered as such, it is preferable to present them as a pharmaceutical formulation. The formulations, both for veterinary and for human medical use, of the present invention comprise the free fatty acids as defined, together with one or more pharmaceutically acceptable carriers therefore and, optionally, other therapeutic ingredients, although other unsaturated fatty acids should be avoided. The carriers must be pharmaceutically acceptable in the sense of being compatible with the other ingredients of the formulations and not deleterious to the recipient thereof. Formulations include those suitable for oral, rectal, vaginal, intrapulmonary, or parenteral (including subcutaneous, intramuscular, and intravenous) administration. Formulations for oral administration, such as tablets or capsules, are preferred.

The free fatty acids of the present invention may also be administered by replacing butter and/or ordinary margarine by a special margarine, e.g., of the emulsion type, formulated so that in normal usage the recipient would receive the required amount of the combination. Cooking oils and fats may also be similarly formulated to contain the composition of the present invention.

The EPA and DHA are separated from fish oil such as cod liver oil as described in copending application Serial No. 810,550, entitled "A Method of Extraction and Purification of EPA and DHA from Natural Sources", now U.S. Pat. No. 4,792,418 the entire contents of which are hereby incorporated by reference.

The free fatty acids are obtained by first hydrolyzing the triglycerides of the oil source under mild conditions, such as by the use of the enzyme lipase, removing non-saponifiable material by washing with organic solvent, treating with urea in order to remove saturated and mono-unsaturated fatty acids to form a urea complex with saturated and mono-saturated fatty acids, dissolving the remainder in an organic solvent, preferably acetone, slowly cooling and fractionally removing solidified material as it forms. In a preferred embodiment, the use of extremely low temperatures to complete the precipitation of the pure fatty acids can be avoided by increasing the concentration of fatty acid in the solution after the formation and removal of each precipitate by evaporating a proportion of the solvent and then repeating the cooling step. In this manner, substantially the same yield and purity can be obtained without the use of extremely low temperatures which would make a commercial process less desirable.

The oil from which the EPA and DHA is separated by means of the present invention is preferably as fresh as possible so that the separation may occur before any substantial degradation of the fatty acids occurs. Natural fats or oils containing high levels of EPA and DHA suitable for use in the present invention include, for example, fats and oils of marine animals such as colored fish, such as the mackerel, sardine, mackerel pike and herring; cod liver oil; and marine animals such as krill and the various shrimp-like animals. It should be understood, however, that any source of EPA and DHA may be used in the present invention. Preferably, the source fish are obtained from as cold an environment as possible. The optimal enzymatic activity for the enzyme $a^5$-desaturase, which catalyzes the conversion of eicosatetraenoic acid to EPA, occurs at 9° C. Thus, fish from cold environments are higher in EPA than warmer water fish.

Furthermore, even greater yields of EPA can be obtained if the fish are raised in a controlled environment. If the fish are fed a diet rich in α-linolenic acid and maintained in salt water at 9° C., optimum amounts of EPA will be produced.

The natural fat or oil is subjected to saponification or alcoholysis in order to convert the triglycerides to free fatty acids or esters of fatty acids. The method selected, however, should be one in which high temperatures and strongly basic reagents are avoided, as these can lead to peroxidation and cis-trans conversion. The preferred method of hydrolysis is enzymatic hydrolysis using the enzyme lipase at a temperature of 35–40° C. and pH of 6–7. The lipase should be activated by traces of cysteine or ascorbic acid, as is conventional. Another advantage of the use of lipase for saponification is the fact that lipase enzyme, being stereo-specific, will not cleave any trans-fatty acids, which may be produced in nature from the triglycerides. Thus, even if there is trans-EPA or DHA in the starting material, it will be removed with the non-saponified material and will not be present in the final product.

An alternative method of hydrolyzing the natural fats and oils is by partially hydrolyzing these fats and oils with lipase or a strong base. When lipase is used, hydrolysis for 1½ to 2 hours, rather than for the usual six hours, provides a richer source of EPA because the lipase preferentially removes the first and third branches of the treated triglyceride. It is known that in natural triglycerides the outside branches have more greatly saturated chains than the middle branch. Thus, limiting the amount of hydrolysis automatically removes a substantial amount of the more saturated acids.

Potassium hydroxide can also be used to partially hydrolyze the natural fats or oils. The source of oil is treated with potassium hydroxide for about 15–20 minutes to partially hydrolyze the triglycerides. As in the case with lipase, this partial hydrolysis yields a richer source of EPA from the triglyceride because the first and third branches of the triglyceride are preferentially attacked by the base.

After the partial hydrolysis, sulfuric acid or other strong mineral acid such as hydrochloric acid or nitric acid is added to the hydrolysis mixture to separate out the mixture of fatty acids. The mixture of fatty acids floats to the top, and the bottom, aqueous, phase is discarded.

This partial hydrolysis step is also useful in improving the separation of other polyunsaturates from their triglycerides, regardless of the source of the triglycerides.

Mixtures of free fatty acids can also be separated from their natural sources by a transesterification process. The fatty acid containing material, e.g., marine animal oil, is refluxed with dry ethanol or dry methanol and a trace amount of sodium metal. This forms the ethyl or methyl esters, respectively, of the free fatty acids, liberating them from the triglyceride molecules. This method involves substantially milder conditions than basic hydrolysis, and prevents darkening of the reaction mixture from harsh conditions. The esters can be converted to free fatty acids at any stage of the extraction procedure by standard hydrolysis techniques. For some purposes it may be desirable to use the esters directly without conversion to the free acid form.

In the next step, the non-saponifiable materials, such as cholesterol, vitamins A and D and hydrocarbons, are removed by washing with an organic solvent. Any organic solvent, such as petroleum ether, methylene chloride, ethyl ether, etc., may be used for this purpose.

After removal of the organic phase, the aqueous phase is acidified. Any acid may be used for this acidification step, although pharmaceutically acceptable acids are preferred. This will cause the free fatty acids to separate into a separate organic phase. The aqueous phase is then discarded. The addition of a small amount of sodium chloride or other salt will enhance the separation.

The fatty acid mixture is next submitted to a urea treatment in order to remove saturated and mono-unsaturated fatty acids. In the urea treatment, urea is added to a polar organic solvent capable of readily dissolving both urea and the fatty acids therein. Examples of operable solvents include methanol, ethanol, isopropanol, petroleum ether, benzene, trichloroethylene, and methyl isobutyl ketone. Ethanol is preferred in order to avoid toxicity problems. The urea is dissolved in the solvent, if necessary with heating, to obtain a urea solution which normally contains from 10 to 20% of urea. The urea solution and the fatty acid mixture are mixed together. While the fatty acid mixture may be added to the urea solution, it is preferred that the fatty acid mixture first be diluted in additional organic solvent in order to provide some degree of protection for the fatty acids against the elevated temperature of the urea solution. The free fatty acids may be dissolved in petroleum ether or other polar solvents such as acetone, ethanol, or methanol. The amount of the urea solution is adjusted to be at least 0.5 parts by weight, preferably 1–4 parts, relative to each part by weight of the fatty acid mixture. The urea solution is mixed homogeneously with the fatty acid mixture.

The urea is then precipitated, preferably by cooling the urea-treated solution. At this time, saturated and mono-saturated fatty acids in the fatty acid mixture will form a complex with the urea crystals and precipitate out. The cooling may be conducted by leaving the solution to stand for a long period of time, if desired. The solution may also be forcibly cooled, for example by use of a water bath. Good results will be obtained when the solution is cooled to a temperature of at most 50° C., preferably from 30–40° C. To obtain an even better urea removal, the solution may be further cooled in a refrigerator to about −10° C.

The complex of urea with saturated and mono-unsaturated fatty acids is then filtered off or otherwise removed. The filtrate solution obtained is concentrated, for example in an evaporator, to remove the major portion of the solvent, and then any remaining urea is washed from the fatty acid mixture with 5% hydrochloric acid. The solvent may also be removed by water extractions using 10 parts of water to one part of solvent.

The remaining fatty acid mixture is a substantially pure combination of higher unsaturated fatty acids. It has been discovered that these individual fatty acids may be completely separated in a very simple and accurate method by first dissolving them in an organic solvent, such as acetone, and then gradually cooling until the desired fatty acid solidifies out of the solution. As the solution is gradually cooled, various fatty acids, depending on their individual solubility in the solvent, precipitate. As each of these fatty acids precipitates, it is removed from the solution. The various fatty acids have specific points at which they precipitate from solution, depending upon their concentration in the solution. For example, it has been discovered that DHA precipitates from a 10% acetone solution at about −38° to −40° C. EPA precipitates at about −60° C. Most other fatty acids precipitate at temperatures above −30° C.

The solution is cooled in a bath of frozen carbon dioxide (dry ice) in acetone. The precipitate which forms at −38° to −40° C. is removed by filtration through sintered glass or a Buchner funnel without substantially raising the temperature. Analysis of the obtained crystals shows substantially pure DHA; NMR studies show no cis-trans conversion.

The substance precipitating at about −60° C. has been shown to be substantially 100% pure EPA with no cis-trans conversion.

In order to avoid the extremely low temperatures required to separate EPA and DHA separately, the volume of the supernatant can be reduced after each crystallization to reduce the solubility of the fatty acids, yielding a mixture of substantially pure DHA and EPA.

The solvent reduction method of low temperature fractional crystallization may be accomplished using the combination of higher unsaturated fatty acids which are obtained as a result of the urea treatment step discussed in detail above. The combination of higher unsaturated fatty acids obtained by the urea treatment step is dissolved in the same type of organic solvent as is used for the reducing temperature method; for example, is to be placed into a 10% solution of acetone or petroleum ether. When cooled overnight to about −20° C., any remaining saturated fatty acids and various fatty acids with low degree of unsaturation solidify out of the solution. The precipitate is then removed and discarded. The solution is then reduced in volume and increased in concentration by evaporation or distillation of the solvent to a predetermined fraction of its original volume, for example, one third of its original volume. When the reduced volume solution is again cooled to about −20° C., new crystals of mono-unsaturated fatty acids appear which crystals are again filtered out. The filtrate may then again be reduced by a factor of about one half to one ninth of its original volume and again cooled overnight to −20° C. Di-unsaturated fatty acids will now solidify out of solution. These crystals may again be filtered out and discarded.

To be sure that all undesired fatty acids have crystallized from the solution, the filtrate may be cooled further to −30° C. If no crystals appear, then the purification is complete. The solvent may then be evaporated.

The remaining liquid consists of a substantially pure combination of EPA and DHA. If desired, these two components may be separated by cooling to −38° to −40° C. to precipitate the DHA.

Patients suffering from rheumatoid arthritis were treated with sardine oil containing EPA and DHA in the triglyceride form, and with sardine oil after hydrolysis of the acids and removal of the glycerine. The study was conducted for 25 days. Each patient took three teaspoons per day, and did not change his dietary habits or medications in any way. The control group was administered three teaspoons of peanut oil each day.

During the test period, the patients were tested for erythrocyte sedimentation rate. The erythrocyte sedimentation rate was taken according to the Westergren method, considered to be the most objective and reliable measurement for the disease activity. The lower the sedimentation rate, the less active is the disease. Values from about 20-35 are considered to be normal.

The results of the test are tabulated below.

| | The effect of fish oil (sardines) and Free fatty fish oil acids on Rheumatoid Arthritic patients (Sedimentation Rate)* | | | | | |
|---|---|---|---|---|---|---|
| | Control peanut oil | | Fish oil (Triglyceride) | | Free Fatty acid | |
| | Before Study | After 25 days | Before Study | After 25 days | Before Study | After 25 days |
| 1 | 90 | 85 | 85 | 60 | 60 | 40 |
| 2 | 60 | 65 | 90 | 55 | 80 | 45 |
| 3 | 65 | 60 | 70 | 60 | 65 | 40 |
| 4 | 70 | 70 | 75 | 60 | 70 | 30 |
| 5 | 85 | 80 | 60 | 60 | 85 | 20 |
| 6 | 80 | 85 | 65 | 45 | 90 | 30 |
| 7 | 70 | 60 | 80 | 70 | 75 | 35 |
| 8 | 75 | 70 | 75 | 70 | 70 | 20 |
| 9 | 80 | 80 | 70 | 40 | 80 | 50 |
| 10 | 60 | 65 | 80 | 60 | 75 | 25 |
| Average | 73.5 | 72.0 | 75.0 | 58.0 | 75.0 | 33.5 |
| S.D. | ±9.8 | ±9.3 | ±8.7 | ±9.0 | ±8.7 | ±9.8 |

*ESR = Erythrolete Sedimantation Rate was taken according to westergren method, considered to be the most objective reliable measurement for the Disease activity. (The lower it gets, the less active is the disease. 20-35 are considered normal values.

It will be obvious to those skilled in the art that various changes may be made without departing form the scope of the invention, and the invention is not to be considered limited to what is described in the specification.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A method for treating rheumatoid arthritis comprising administering to a patient suffering from such arthritis an effective amount of a fatty acid selected from the group consisting of EPA, DHA, and a mixture thereof, said fatty acid being in the free acid form thereof or in the form of a pharmaceutically acceptable salt thereof.

2. The method of claim 1 wherein the fatty acid is EPA.

3. The method of claim 1 wherein the fatty acid is DHA.

4. The method of claim 1 wherein the fatty acid is administered orally.

5. The method of claim 1 wherein the fatty acid is administered parenterally.

6. A method in accordance with 1, wherein the fatty acid is a mixture of EPA and DHA.

7. A method in accordance with claim 1 wherein said fatty acid is the mixture of free fatty acids obtained by hydrolysis of the triglycerides obtained from fish oil to obtain 3 fatty acids and glycerines, and removal of the glycerine.

8. The method of claim 7 wherein said mixture is administered orally.

9. The method of claim 7 wherein said mixture is administered parenterally.

* * * * *